(12) United States Patent
Groscurth et al.

(10) Patent No.: US 11,969,305 B2
(45) Date of Patent: Apr. 30, 2024

(54) EDENTULOUS SURGICAL GUIDE

(71) Applicant: IBUR, LLC, Troy, MI (US)

(72) Inventors: Randall C. Groscurth, Troy, MI (US); Shoko U. Groscurth, Troy, MI (US)

(73) Assignee: IBUR, LLC, Troy, MI (US)

( * ) Notice: Subject to any disclaimer, the term of this patent is extended or adjusted under 35 U.S.C. 154(b) by 196 days.

(21) Appl. No.: 17/400,098

(22) Filed: Aug. 11, 2021

(65) Prior Publication Data

US 2021/0369407 A1    Dec. 2, 2021

Related U.S. Application Data

(63) Continuation of application No. 16/040,527, filed on Jul. 19, 2018, now Pat. No. 11,109,942, which is a
(Continued)

(51) Int. Cl.
*A61C 1/08*    (2006.01)
*A61B 34/10*    (2016.01)
(Continued)

(52) U.S. Cl.
CPC .............. *A61C 1/084* (2013.01); *A61B 34/10* (2016.02); *A61C 1/085* (2013.01); *A61C 8/0001* (2013.01);
(Continued)

(58) Field of Classification Search
CPC ...................................................... A61C 1/084
See application file for complete search history.

(56) References Cited

U.S. PATENT DOCUMENTS

| | | | |
|---|---|---|---|
| 4,917,604 A | * | 4/1990 | Small ..................... A61C 8/003 433/173 |
| 4,998,881 A | | 3/1991 | Lauks |

(Continued)

FOREIGN PATENT DOCUMENTS

| | | |
|---|---|---|
| EP | 0328911 A2 | 8/1989 |
| EP | 1502556 A2 | 2/2005 |

(Continued)

OTHER PUBLICATIONS

English abstract for EP2425796.
(Continued)

*Primary Examiner* — Heidi M Eide
(74) *Attorney, Agent, or Firm* — Fishman Stewart PLLC

(57) ABSTRACT

A method may include obtaining a digital preoperative dental model of a patient, designing a guide appliance set on the digital preoperative dental model according to a surgical plan for the patient, and storing the design of the guide appliance set in a computer-aided manufacturing (CAM) compatible file format. Designing the guide appliance set may include designing a base frame configured to engage an oral structure of the patient without obstructing a planned surgical site region of an alveolar ridge, designing an uppermost surface of the base frame to, at least in an area adjacent to the planned surgical site region, terminate below the alveolar ridge when the base frame is engaged with the oral structure, designing at least one attachment that is releasably attachable to the base frame, and designing the at least one attachment to be fully received in a mouth when attached to the base frame.

20 Claims, 12 Drawing Sheets

Related U.S. Application Data continuation of application No. 15/359,167, filed on Nov. 22, 2016, now Pat. No. 10,034,722, which is a continuation of application No. 13/621,146, filed on Sep. 15, 2012, now Pat. No. 9,504,533.

(60) Provisional application No. 61/535,698, filed on Sep. 16, 2011.

(51) Int. Cl.
 *A61C 8/00* (2006.01)
 *B33Y 80/00* (2015.01)

(52) U.S. Cl.
 CPC ...... *A61C 8/0089* (2013.01); *A61B 2034/105* (2016.02); *B33Y 80/00* (2014.12)

(56) References Cited

U.S. PATENT DOCUMENTS

| | | | | |
|---|---|---|---|---|
| 5,221,204 | A | * | 6/1993 | Kruger .................. A61C 1/084 433/172 |
| 5,641,287 | A | | 6/1997 | Gittleman |
| 5,857,853 | A | | 1/1999 | van Nifterick et al. |
| 6,672,870 | B2 | * | 1/2004 | Knapp .................. A61C 1/084 433/76 |
| 8,529,255 | B2 | | 9/2013 | Poirier et al. |
| 8,926,328 | B2 | | 1/2015 | Suttin |
| 9,375,297 | B2 | | 6/2016 | Davison |
| 10,206,757 | B2 | | 2/2019 | Pettersson |
| 2004/0043355 | A1 | | 3/2004 | Jonsson et al. |
| 2005/0080503 | A1 | * | 4/2005 | Kopelman ............... A61C 5/77 700/118 |
| 2006/0115793 | A1 | * | 6/2006 | Kopelman ........... A61B 5/0002 433/218 |
| 2006/0223029 | A1 | * | 10/2006 | Berger ................. A61C 13/275 433/172 |
| 2008/0166681 | A1 | | 7/2008 | Weinstein et al. |
| 2009/0011382 | A1 | | 1/2009 | Bavar |
| 2009/0298009 | A1 | | 12/2009 | Brajnovic |
| 2010/0075275 | A1 | | 3/2010 | Brajnovic |
| 2010/0124731 | A1 | | 5/2010 | Groscurth et al. |
| 2010/0190137 | A1 | | 7/2010 | Hertz |
| 2010/0203479 | A1 | | 8/2010 | Bulloch et al. |
| 2010/0256649 | A1 | | 10/2010 | Capsal et al. |
| 2011/0045432 | A1 | | 2/2011 | Groscurth et al. |
| 2011/0054656 | A1 | | 3/2011 | Lee et al. |
| 2011/0217667 | A1 | | 9/2011 | Groscurth et al. |
| 2012/0046914 | A1 | * | 2/2012 | Gao ...................... A61C 1/084 703/1 |
| 2013/0172731 | A1 | | 7/2013 | Gole |
| 2014/0272778 | A1 | | 9/2014 | Llop |
| 2015/0010881 | A1 | | 1/2015 | Llop |
| 2016/0157964 | A1 | | 6/2016 | Suttin et al. |
| 2016/0354169 | A1 | | 12/2016 | Suttin et al. |

FOREIGN PATENT DOCUMENTS

| | | |
|---|---|---|
| EP | 2425796 A1 | 3/2012 |
| WO | WO-2009/115617 A1 | 9/2009 |

OTHER PUBLICATIONS

English abstract for EP1502556.

International Search Report for PCT/US2012/055684, dated Nov. 23, 2012.

Patzelt, S.B.M., Emmanouilidi, A., Stampf, S. et al. "Accuracy of full-arch scans using intraoral scanners" Clin Oral Invest (2014) 18: 1687. doi:10.1007/s00784-013-1132-y.

* cited by examiner

EDENTULOUS SURGICAL GUIDE

CROSS-REFERENCE TO RELATED APPLICATIONS

This application is a continuation of U.S. patent application Ser. No. 16/040,527, filed Jul. 19, 2018, which is a continuation of U.S. patent application Ser. No. 15/359,167, filed Nov. 22, 2016 (U.S. Pat. No. 10,034,722, Jul. 31, 2018), which is a continuation of U.S. patent application Ser. No. 13/621,146, filed Sep. 15, 2012 (U.S. Pat. No. 9,504,533, Nov. 29, 2016), which claims priority to U.S. Provisional Patent Application No. 61/535,698, filed on Sep. 16, 2011. The contents of all of the applications are hereby incorporated by reference in their entirety.

FIELD OF THE INVENTION

An improved dental implant method and apparatus is disclosed, and, more particularly, a surgical guide that can be fit to a patient's jawbone.

BACKGROUND AND SUMMARY OF THE INVENTION

Dental implants are commonly used in today's dental practices to support various prostheses. Challenges to the successful placement of dental implants include poor bone quality and various hidden anatomical features such as nerves, roots, and sinus cavities. Surgical preplanning methods and drill guide apparatuses may be used to better address these challenges. With edentulous cases, surgical drill guide apparatuses can be divided into two categories: bone borne surgical drill guides and gum tissue borne surgical guides.

Bone borne surgical drill guides are made to fit on a patient's jawbone, and can be made from either a digital jawbone model or rapid-prototyped physical jawbone model of the patient. The primary problem with bone borne surgical guides is the invasiveness of the amount of flapping of the gum tissue that the surgeon has to create in order for the guide to fit correctly on the patient jawbone. The amount of flapping required increases the likelihood of surgical risks and complications, including blood loss, infection, healing problems, and overall pain experienced by the patient. Flapping and suturing also requires a great deal of surgical time. In addition to the problems associated with the surgical procedure, difficulties may also arise when the jawbone has low density, which happens often with Maxilla bones in posterior region. Low bone density makes it difficult to define the contour of the bone in CT images, which may cause the bone borne surgical drill guide to fit poorly. Thus, the use of bone borne surgical drill guides has drawbacks and it would be preferred to overcome their associated problems.

Gum tissue borne surgical drill guides are made to fit on top of a patient's gum tissue without the need for any surgical incisions to stabilize the guide. In order to create this type of surgical guide, the surface scan data of the gum tissue and the tomography data of the jawbone need to be accurately aligned and mapped. For this purpose, usually an imaging template is worn by the patient during tomography scanning, and the fiducial markers on the device are used for alignment of the different data sets. While this method is less surgically invasive than the bone borne method, gum tissue borne surgical guides lack stability. Gum tissue is in a constant state of movement and drift, and is also pliable with pressure. Moreover, certain health conditions and even the intake of certain foods make gum tissue more prone to swelling. These conditions may prevent the accurate positioning of the device in the mouth. Here, even if the surgeon uses anchor screws, they may be securing the device in the wrong position. This type of surgical drill guide sacrifices accuracy for convenience. Thus, it would be preferred to overcome these problems.

Accordingly, it would be desirable to provide a stable and accurate surgical drill guide apparatus that requires only minimum flapping and fits to both gum tissue and one or multiple small areas of jawbone. Such apparatus may increase the stability of the surgical guide by clasping and/or contacting the jawbone, while improving the overall fit and minimizing the need of flapping by also clasping and/or contacting selected areas of the gum tissue at the same time. The apparatus may be configured to accurately place dental implants according to the planned positions.

It would also be preferable to provide an apparatus that may be custom designed to suit the unique anatomical features of each individual. The device may be designed on a digital anatomical jawbone model with accurately mapped and aligned gum tissue information, and may be rapid prototyped or milled as a drill guide frame or frame set. Also, the apparatus may be made by hand on the rapid prototyped or CNC milled physical anatomical model that partially exposes the jawbone structure.

DETAILED DESCRIPTION OF THE PREFERRED EMBODIMENTS

Figure 1A:
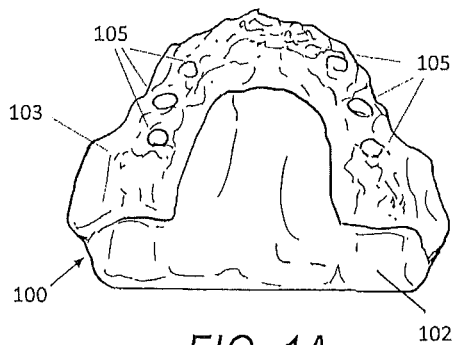
FIG. 1A is a top view of an upper jaw anatomical diagnostic model with gum tissue and a partially exposed bone structure.

Referring now to the discussion that follows and also to the drawings, illustrative approaches are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Figure 1B:
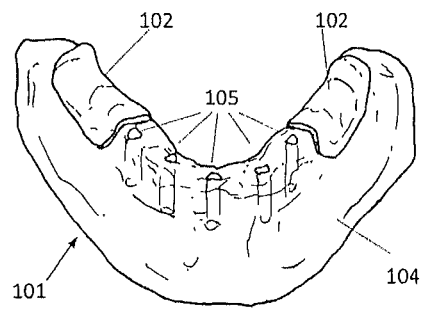
FIG. 1B is a perspective front view of a lower jaw anatomical diagnostic model with gum tissue and a partially exposed bone structure.

FIGS. 1A and 1B illustrate patient specific digital or physical dental anatomical diagnostic models 100 and 101 that expose the partial upper jawbone bone structures 103 and a lower jawbone 104 at the surgical sites and the areas of interest. In areas where the bone structures are not exposed, the model has gum tissue surface structures 102. As in FIGS. 1A and 1B, these gum tissue surface structures 102 usually appear towards the distal end of the posterior regions and the palatal area of the upper jaws.

Figure 1C:
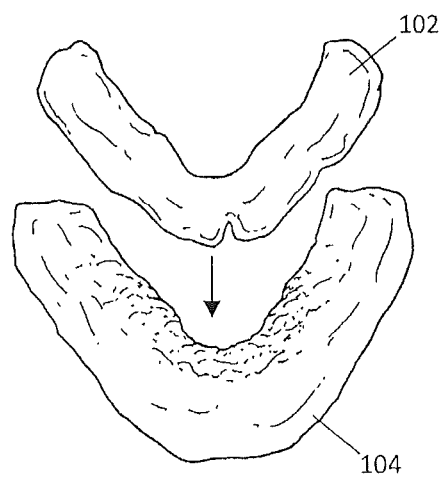
FIG. 1C is a perspective front view of a lower jawbone digital image and a gum tissue image which are about to be aligned.
Figure 1D:
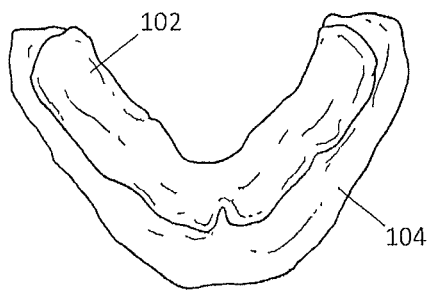
FIG. 1D is a perspective front view of a lower jaw bone digital image aligned with the gum tissue digital image.

FIGS. 1C and 1D depict a digital image of a lower jawbone 104 and a digital image of the gum tissue surface structures 102 positioned relative to one another, from which diagnostic anatomical models like 1A and 1B are created.

The bone structure data can be obtained by tomography imaging devices such as CT and CB CT, and may be exported as a file format, such as STL, suitable for reverse engineering and 3D imaging. Then the data file can be accurately aligned with the surface scan data of the gum tissue 102 obtained by devices such as laser and optical scanners by means of matching fiducial markers on the imaging apparatus that the patient wears during the tomography scan to the markers' positional information on the surface scan data. If the bottom of the apparatus represents the patient's gum tissue surface, the image of the patient's gum surface can also be obtained by scanning the imaging apparatus alone using a tomography device. In this case, these two CT data files can be aligned by the fiducial marker location(s) after each structure is thresholded and is exported as a proper file format for modeling. If a radio opaque duplicated denture is used as an imaging apparatus, the bone structure data and the gum surface data can be obtained with a single CT scan of the patient with the imaging apparatus in place. After the necessary structures are properly aligned in a file format suitable for 3D modeling, the data files can be combined and used to design a digital anatomical diagnostic model with a partially exposed bone structure in the area of the surgical site.

The osteotomies of simulated dental implant placements 105 may be created either digitally on the digital anatomical diagnostic model or manually on the rapid-prototyped physical anatomical diagnostic model. Then a drill guide apparatus may be designed on this type of digital anatomical diagnostic model so that it will accommodate drill guide bushings or holes which guide the surgical drill according to the planned osteotomies either on the digital anatomical diagnostic model or the physical anatomical diagnostic model. Alternatively, the whole apparatus can be designed manually on this type of physical anatomical diagnostic model with dental materials such as, but not limited to, light cured composite, cold cured resin or acrylic, or thermoplastic.

Figure 2A:
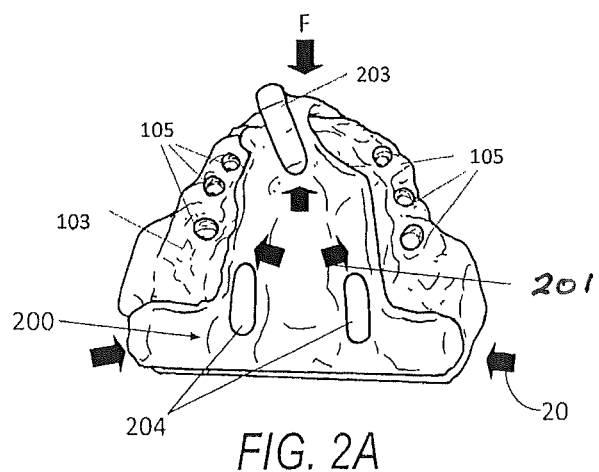
FIG. 2A is a top view of an exemplary base frame for an upper jaw on a diagnostic model with gum tissue and a partially exposed bone structure.
Figure 2B:
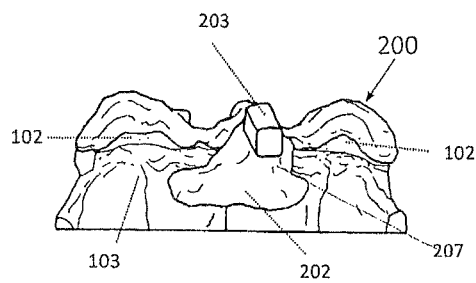
FIG. 2B is a side view of the exemplary base frame for the upper jaw on FIG. 2A diagnostic model.
Figure 2C:
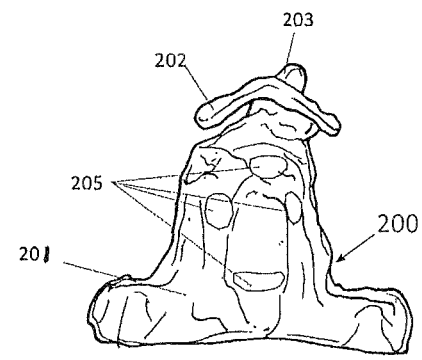
FIG. 2C is a bottom view of the exemplary base frame for the upper jaw shown in FIG. 2A.
Figure 2D:
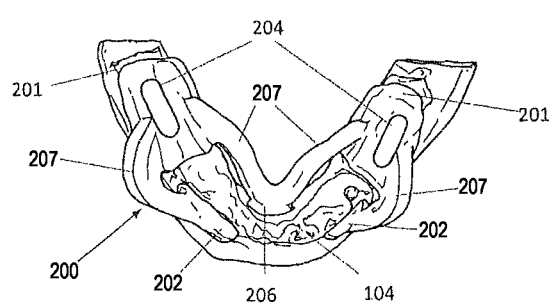
FIG. 2D is a top view of an exemplary base frame for a lower jaw on a diagnostic anatomical model with gum tissue and a partially exposed bone structure.
Figure 2E:
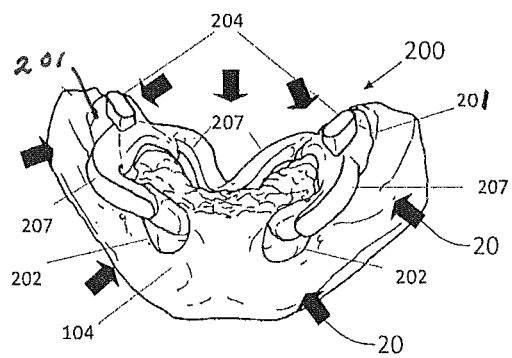
FIG. 2E is a perspective front view of the exemplary base frame for the lower jaw on the same anatomical diagnostic model shown in FIG. 2D.

FIGS. 2A-E are exemplary designs of a base frame 200 for an upper jaw (FIGS. 2A-2C) and a lower jaw (FIGS. 2D & 2E). The base frame 200 may be made of a transparent or semi-transparent resin or other composite material that gives the surgeon maximum visibility of the surgical site, but it may also be made of a colored resin and other composite material or metal that provides the base frame 200 with enough rigidity for stability and the right amount of flexibility in clasping areas. In order to obtain rigidity and flexibility in different areas, the frame 200 may be designed to have thick areas and thin areas accordingly within the frame. Overall however, the base frame can be more flexible than one piece surgical guide since the surgical drill guide section placed on top of it can solidify the whole drill guide assembly and the flexibility allows the device to clasp on to the undercut easily. The base frame 200 is shown positioned on top of the upper jawbone structure 103. A plurality of osteotomies of simulated dental implant placements 105 are shown about the periphery of the upper jawbone structure 103. A handle 203 is secured towards a forward portion of the base frame 200 which is used to aid in the maneuverability of the base frame 200. Interlocking connectors 204 are firmly mounted to, or formed part thereof, the base frame 200, and provide guides for the surgical drill guide housing frame 300 to connect thereto. The arrows 20 depict potential pressure impinging points for the drill guide housing frame 300 to impinge upon.

FIG. 2D shows a base frame 200 on the type of anatomical models explained above, and gum tissue contact portions 201 are placed on the gum tissue areas of the model. Although this portion may have broad area contacts with the gum tissue 102, it may also have strategically placed smaller spot contact areas 205 as shown in FIG. 2C. In some designs, certain areas of gum tissue contact portion can be used to place temporary anchors through the gum tissue into the patient jawbone by small screws, pins or other fastening devices.

The surgical device 200 may also have one or more clasping lateral contacts 202 (See FIGS. 2B-2E) that may simply contact the lateral wall of the exposed jawbone 103 and 104 or engage its undercut. As shown in one exemplary design of the base plate 200 for a lower jaw 104 (FIGS. 2D & 2E), clasping lateral contacts 202 may be connected to the gum tissue contact portion 201 by stabilizing/clasping arms 207 that may or may not have contact with the oral structure. The stabilizing/clasping arms 207 extend out from a base frame 200 and/or drill guide housing frame 300 which may be turn into a drill guide housing section 400 with drill guide bushings. When the frame is placed on the oral structure or anatomical diagnostic model, the stabilizing/clasping arms 207 slightly flex out and then clasp securely onto the oral structure 104. Although the stabilizing/clasping arms 207 are illustrated as peninsulas that extend out of the tissue contact area, the stabilizing/clasping arms 207 may be continuously connected to the tissue area like in the exemplary base frame 200 shown in FIG. 2F. Clasping lateral contact area 202 may also be used for placing a temporary anchor directly into the jawbone 104 if the patient's oral structure does not allow the device to have enough retention.

Figure 12:
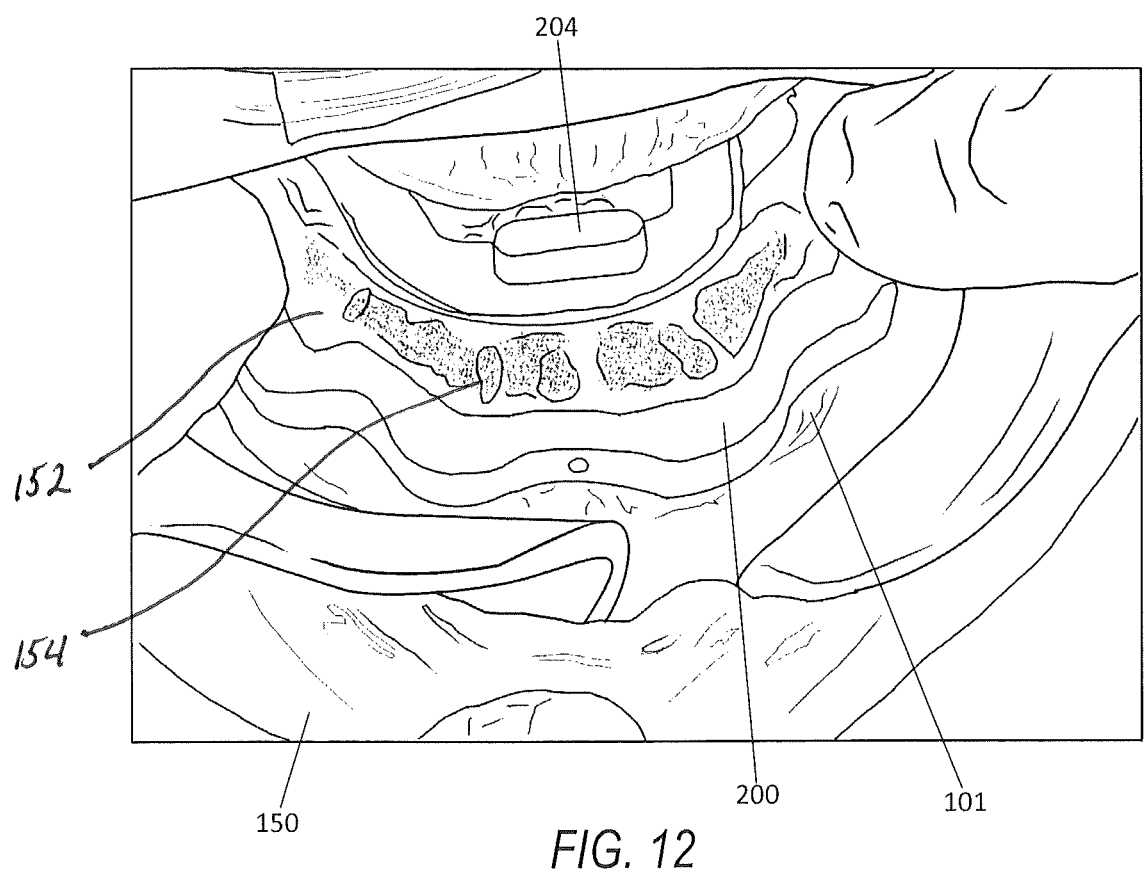
FIG. 12 is the base frame of the FIG. 9 drill guide assembly shown positioned within the mouth of a patient.

Similar to the clasping lateral contacts 202, one or more occlusal/lateral stabilizing rests 206 (FIG. 2D) may be strategically placed to contact the jawbone 104 to work along with the gum tissue contact portion 201 and the clasping lateral contact 202 in order for the device 202 to be securely positioned inside of the patient's oral structure (See FIG. 12). This section may also be connected to the gum tissue contact portion 201 by at least one stabilizing/clasping arm 207.

Figure 6A:
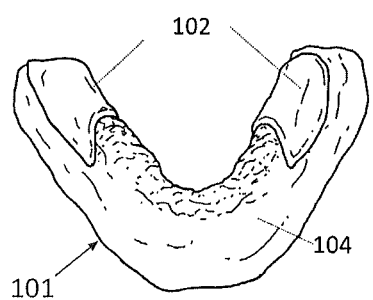
FIG. 6A is a perspective front view of an exemplary anatomical diagnostic model with a partially exposed lower jaw bone before adjustment.
Figure 6B:
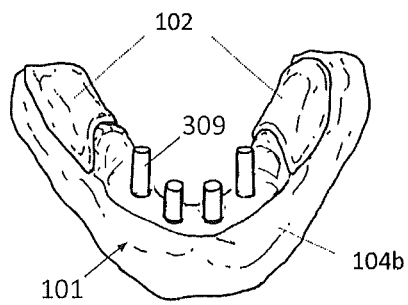
FIG. 6B is a perspective front view of the exemplary anatomical diagnostic model with a partially exposed modified lower jaw bone with planned osteotomies.
Figure 6C:
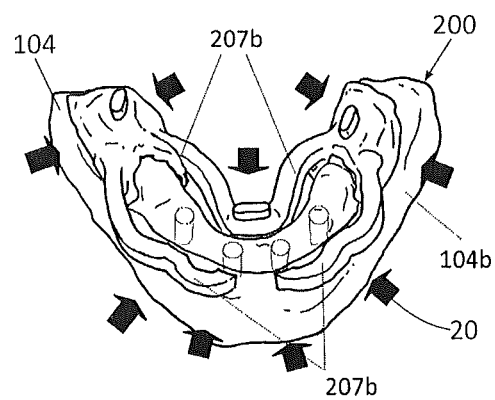
FIG. 6C is a perspective front view of an exemplary base frame on the diagnostic anatomical model.

The arrows on FIGS. 2A, 2E and 6C indicate the direction of force 20 applied from each contact point to the oral structure, and show how stabilizing/clasping arms 207 help fixate the device 200 in place.

Although it is not illustrated, due to a particular shape of the jawbone 103, 104, the base frame 200 may be designed to have only tissue contacts without any jawbone contact and to have a separate detachably attachable part that snaps onto it and engage the jawbone. Alternatively, this bone clasping part can be a latch connected to the base frame 200 by a hinge.

Figure 2F:
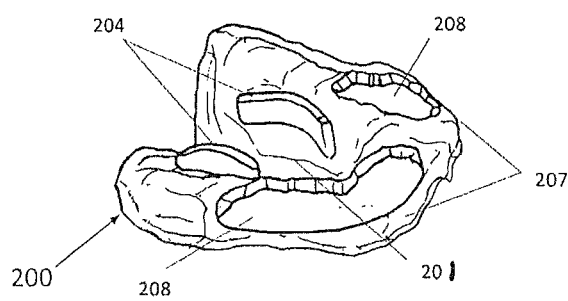
FIG. 2F is a perspective view of an exemplary base frame for the upper jaw.

The base frame 200 may also include a handle 203 on FIGS. 2A-2C that may be used when removing the device from the oral structure, and an interlocking connector 204 (FIG. 2A, 2B, 2D, 2E) that securely connects the base frame 200 to a surgical drill guide housing frame 300 (FIGS. 3A-3E, and FIGS. 4A, & 4C). The handle 203 may also be a handle/connector, a part of which works as a male interlocking connector. FIG. 2F illustrates the base frame 200 having connectors 204 that are secured to the upper service thereof. Stabilizing arms 207 are positioned around its outer periphery with openings 208 being positioned adjacent thereto.

Figure 3A:
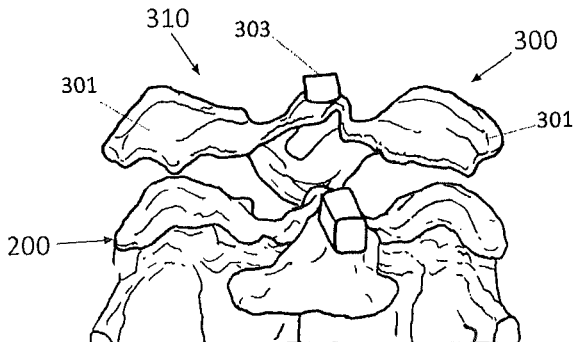
FIG. 3A is a side view of the exemplary drill guide housing frame for the upper jaw about to be attached to the exemplary base frame on the anatomical model.

FIG. 3A illustrates an exemplary drill guide housing frame 300 configured to be disposed on the base frame 200, which collectively form an assembly 310. Material requirements for the drill guide housing frame 300 are same as the specifications for the base frame 200. The drill guide housing frame 300 may securely snap onto the base frame 200 by the interlocking connectors 204 (FIGS. 2A, 2C, 2D, 2E) and the connector receptors 304 (FIG. 3B), also by the handle 203 and handle/connector receptors 303 (FIGS. 3A-3D), along with various stabilizing rests and/or clasping contact areas between the two devices 200, 300. As illustrated, the interlocking connectors 204 on the base frame 200 may be male connectors with strategically placed slight undercuts, and the connector receptors 302 and 303 on the drill guide housing frame 300 may be female connectors. However, various types of different connector mechanisms can be used for this purpose. Similar to the handle/connector 203 on the base frame 200, the handle/connector receptor 303 may be used when removing the device from the base frame 200, and it may also be used as a receptor for the handle/connector 203. Similar to the contact points/areas of the base frame to the oral structure, the drill guide housing frame 300 may have clasping or resting contact points/areas to the base frame 200 besides the connectors. These contact points/areas may be strategically placed to work together along with the connectors not only to ensure a secure fit of the part to the base frame 200 but also to lock in the entire device (the base frame and the drill guide housing section) onto the oral structure by adding an extra layer of thickness and applying more clasping force. The base frame 200 and the surgical drill guide housing 300 may be designed to work together to make the assembly 310 set snugly fit onto the oral structure 100 and yet have great rigidity so that it is very stable in the patient's mouth as well as on the physical anatomical diagnostic model. Although not illustrated, the frames may be fastened together using any other suitable fasteners including, but not limited to, screws, pins and latches.

Figure 3B:
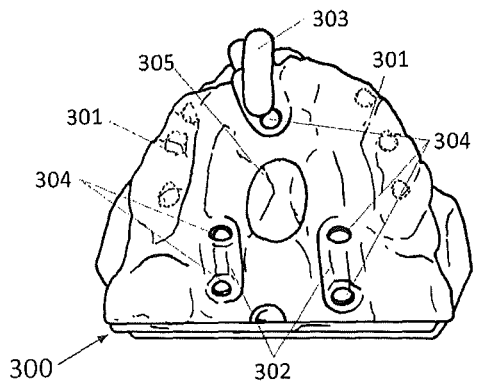
FIG. 3B is a top view of the FIG. 3A drill guide housing frame, with skirted area on the base frame and the physical anatomical diagnostic model.
Figure 3C:
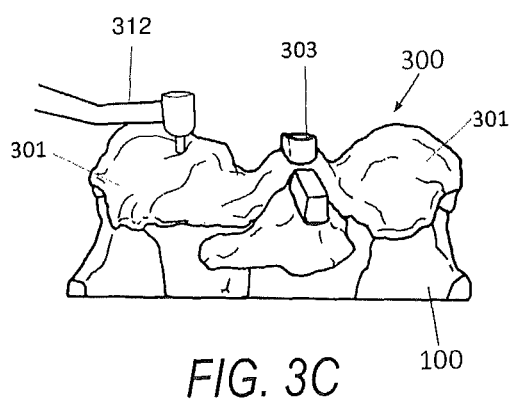
FIG. 3C is a side view of the FIG. 3A drill guide housing frame, with a hand piece drilling holes into the skirted areas.
Figure 3D:
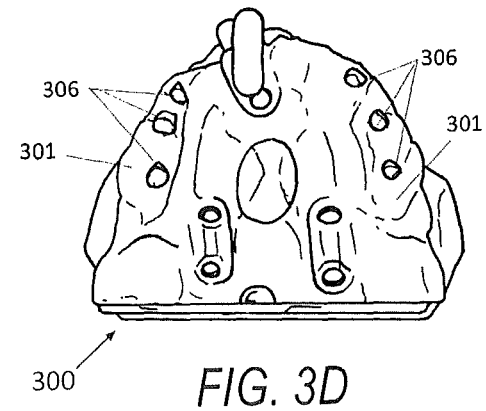
FIG. 3D is a top view of the FIG. 3A exemplary drill guide housing frame, with holes that correspond with planned osteotomies on the physical anatomical diagnostic model.
Figure 4A:
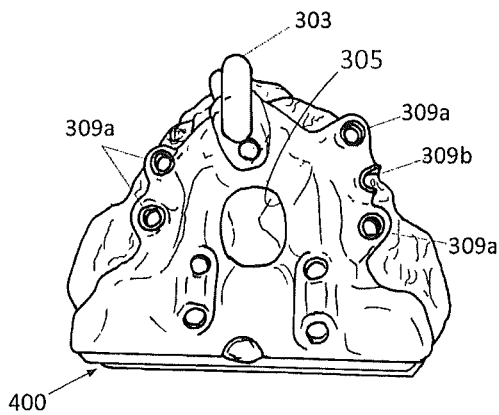
FIG. 4A is a top view of an exemplary drill guide section for the upper jaw placed on the base frame and the physical anatomical diagnostic model.
Figure 4B:
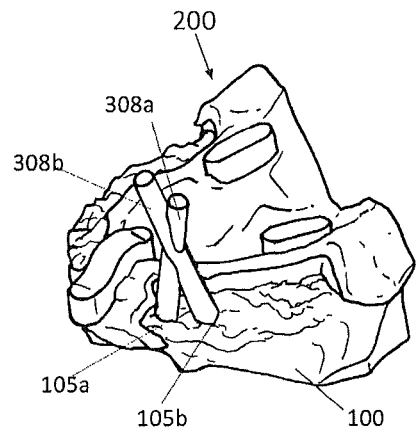
FIG. 4B is a perspective view of the FIG. 4A anatomical diagnostic model with base frame and positioning pins, showing intersecting osteotomy angulations.
Figure 4C:
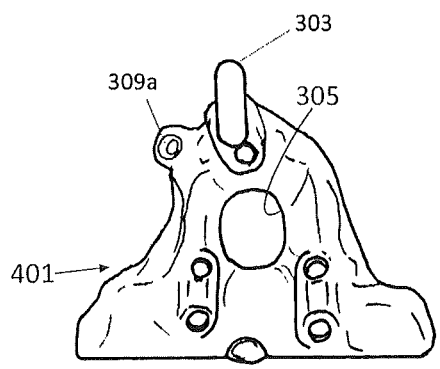
FIG. 4C is a top view of an exemplary interchangeable additional drill guide section with a tube surgical drill guide bushing.

The holes 304 on the connector receptors 302 and handle/connector receptor 303 shown on FIGS. 3B and 3D are liquid escape holes 304 that allow excess moisture and debris to escape so that they will not be trapped in-between the devices 200 and 300. It should be noted that the liquid escape holes 304 can be created in different areas of the drill guide housing frame 300. The larger opening holes 305 in the middle of the devices 300 and 401 in FIGS. 4A and 4C are clearance openings for fastening anchor devises such as screws and pins that are used to fasten the base frame 200 onto the jawbones 103 and 104 without engaging with the drill guide housing frame 300. However, the larger opening holes 305 may also be used as liquid escape holes 304.

Unlike the handles 203 and 303, other exemplary handles may not have a connecting function. The handles may be on either one or both of the base frame 200 and the drill guide housing frame 300, and there may be more than one handle 203 and 303 on both frames. Moreover, the handles on the base frame 200 and the drill guide housing frame 300 can work together as a combination handle unit. Ideally, the combination handle unit is designed to leave a small space at least in a certain area between the devices' handles so that a hand instrument or other types of tools can be inserted into the space to pry the frames apart. Also, similar spaces 601 for the instrument may be created between the frames in other areas to make the separation of the frame easier. See FIGS. 6D, 8 and 11.

Figure 3E:
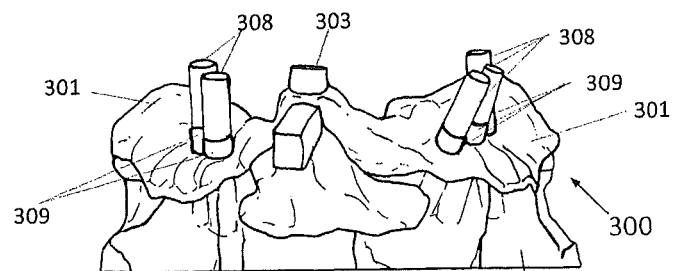
FIG. 3E is a side view of the FIG. 3D physical anatomical diagnostic model, with positioning pins and drill guide bushings placed into the planned osteotomies through the holes on the skirt portion of the drill guide housing frame.

Optionally, the device may also feature skirted areas 301 (FIG. 3B) over the intended surgical site(s). This feature may be useful when the surgeon plans the osteotomies 105 on a physical anatomical model and the device is rapid prototyped or CNC milled from the design created on the digital anatomical model. The skirted areas may be a thin shell that extends from the device 300 and covers the intended surgical site(s). The purpose of this feature is to provide base structure for the surgical drill guide site(s). When the osteotomies are planned on a rapid-prototyped or milled physical anatomical model, the implant positions and angulations are unknown at the time of manufacturing of the surgical drill guide frame or frame set. By having a thin skirted area 301 over the intended implant site as a base structure, it may be easier to prepare the surgical drill guide site(s) on the device 300. Also, the skirted area 301 can be made so that the top surface or the bottom surface of the section represents the patient's gum tissue 102. It can also be made so that the bottom surface of the section sits on top of the bone, a certain distance away from the bone below or above the gum tissue. By going through the procedure that is shown on FIG. 3C, the holes 306 that correspond with the planned osteotomies 308 will be created on the skirt as shown on FIG. 3D. Drill 312 is used to create the holes 306. When the surgical drill guide sites are prepared on the physical anatomical model 100, positioning pins 308 may be used to set the angulations of the osteotomies and to position the surgical drill guide parts 309 as shown in FIG. 3E.

Figure 4D:
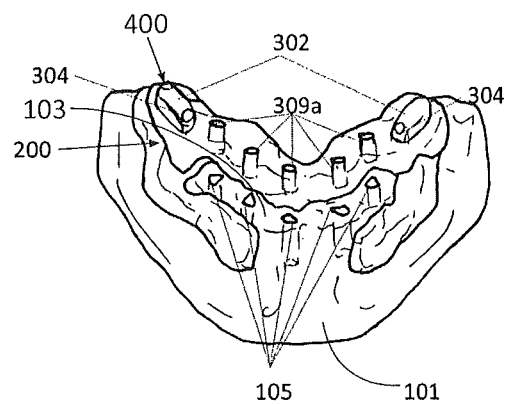
FIG. 4D is a top view of an exemplary surgical drill guide section for the lower jaw placed on the base frame and the physical diagnostic anatomical model.

FIG. 4A illustrates an exemplary surgical drill guide section 400 that was trimmed after surgical drill guide sites are prepared so that the device 400 may provide improved surgical site visibility and good facility for irrigation. Optionally, metal or ceramic tube type 309a or open-face type 309b surgical drill guide bushings can be attached to the device 400, but the device may not have any added parts to the drill guide site. If the implant placement is digitally planned on the digital anatomical model prior to the model manufacturing, the drill guide housing frame 300 can be digitally designed like this illustration, without any skirted area 301, so that the drill guide bushings 309a and 309b can be attached to the device 400 right after manufacturing. Another exemplary surgical drill guide section 400 shown in FIG. 4D for a lower jawbone 101 snapped on to the base frame 200 illustrates the space 105 between jawbone surface 103 and the bottom of the drill guide housing frame 400 over the surgical site, which may be preferred by surgeons for the better irrigation. However, as previously described, the bottom surface of the drill guide housing frame may be set at a different height.

Figure 5:
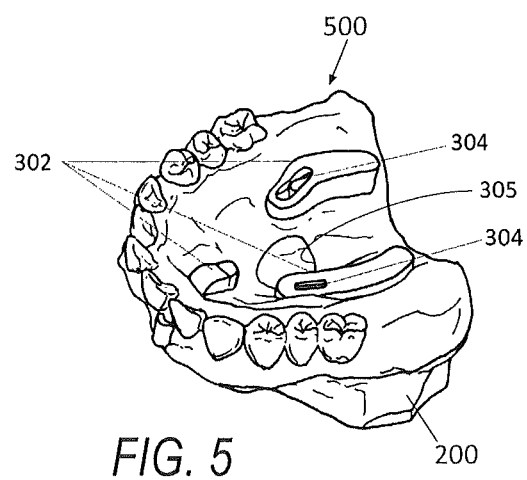
FIG. 5 is a perspective view of an exemplary modified denture duplicate attachment for an upper jaw attached to a base frame.

FIG. 5 illustrates the modified duplicated denture appliance 500 attached to the base frame 200. One way of creating this appliance is to scan the patient's denture or duplicated denture surfaces, align the data to the anatomical model, and modify it to fit on the base frame 200. This appliance 500 may have features such as connector receptors 302, irrigation holes 304, and openings for fastening anchor devices 304 just like a surgical drill guide housing frame 300. This appliance 500 may be used to verify the position of the base frame or the single piece surgical guide with patient's bite. Other examples of attachments include, but are not limited to, an implant pick up impression tray, an implant transfer jig tray, and a bone adjustment jig.

Advantages of the drill guide assembly 310 having the base frame 200 and the drill guide housing frame 300 may include: 1) Interchangeable multiple guide frames 300 can be used during the surgery while the base frame 200 can be securely positioned in the patient oral structure; 2) If, for any reason, the doctor changes the positioning of one or more of the implants from the original plan, and cannot use the surgical drill guide for those particular site(s), or needs to work on the bone, he/she can temporarily remove the drill guide housing frame 300 from the base frame 200 without disturbing the position of the base frame 200; 3) Various types of additional attachments can be placed on the base plate 200 without the drill guide parts covering the surgical sites. The drill guide assembly 310 is especially beneficial when the base frame needs to be temporarily anchored to the patient's jawbone.

More than one surgical drill guide section 400 may be needed in order to accommodate a surgery's specific needs. As illustrated with the positioning pins 308a and 308b in FIG. 4B, two of the intended osteotomies 105a and 105b are very close to each other and have intersecting positioning angulations. In this case, a second surgical drill guide section, 401 in FIG. 4C may be created for one of the planned osteotomies 105a. This type of additional surgical guide section 401 is detachably attachable to the base frame 200 and is interchangeable with the first surgical drill guide section 400. Alternatively, smaller parts that house the surgical drill guide bushings 309 or drill guide holes for specific implant placement sites may be attached to the first surgical drill guide section 400. Although it is not illustrated, another benefit for having additional surgical drill guide section 401 is to accommodate larger size surgical drill guide bushings, 309a and 309b that are subsequently used for finish drilling osteotomies 105.

FIGS. 6A-6D represent a situation in which the doctor decides to reduce the jawbone prior to implant placement. FIG. 6A is an anatomical diagnostic model of a lower jaw 101 which shows a gum tissue portion 102 and a partially exposed bone structure 104. The doctor may wish to modify the bone 104b prior to the implant placement as in FIG. 6B. In this case, the base frame 200 (FIG. 6C) may be designed according to the doctor's specification either on the digital model or the physical anatomical diagnostic model so that it can be used as a bone reduction jig. FIG. 6C illustrates a base frame (200) on an anatomical diagnostic model with a modified lower jawbone 104. A drill guide section 400 FIG. 6D may be designed on top of the base frame 200 to be used for implant placement.

Various types of additional detachably attachable appliances can be added to the surgical drill guide 400. One example of an additional appliance is a modified duplicated denture attachment 500.

Figure 7:
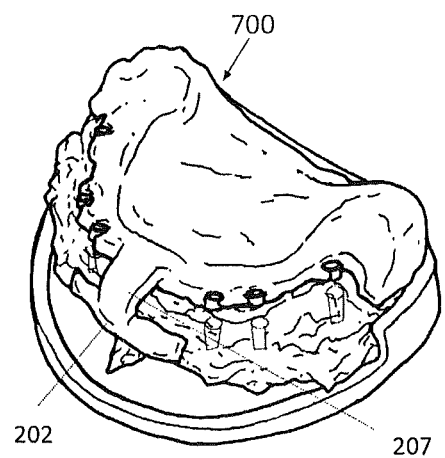
FIG. 7 is a perspective view of an exemplary one piece drill guide on a physical anatomical diagnostic model.

It will be appreciated that the surgical drill guide can be manufactured as single piece 700 (FIG. 7) that contacts both gum tissue and exposed bone. Single piece apparatus 700 has combined functions of both base frame 200 and the surgical drill guide section 300. The device may have all or some of the features described above, or it may include different types of attachments. Lateral contacts 202 on the forward edge are connected to an arm 207, which may be a part of the single piece guide 700.

Figure 6D:
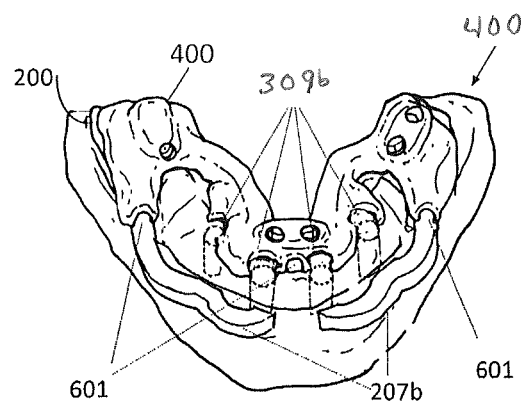
FIG. 6D is a perspective front view of an exemplary drill guide section placed on the base frame and the anatomical diagnostic model.
Figure 8:
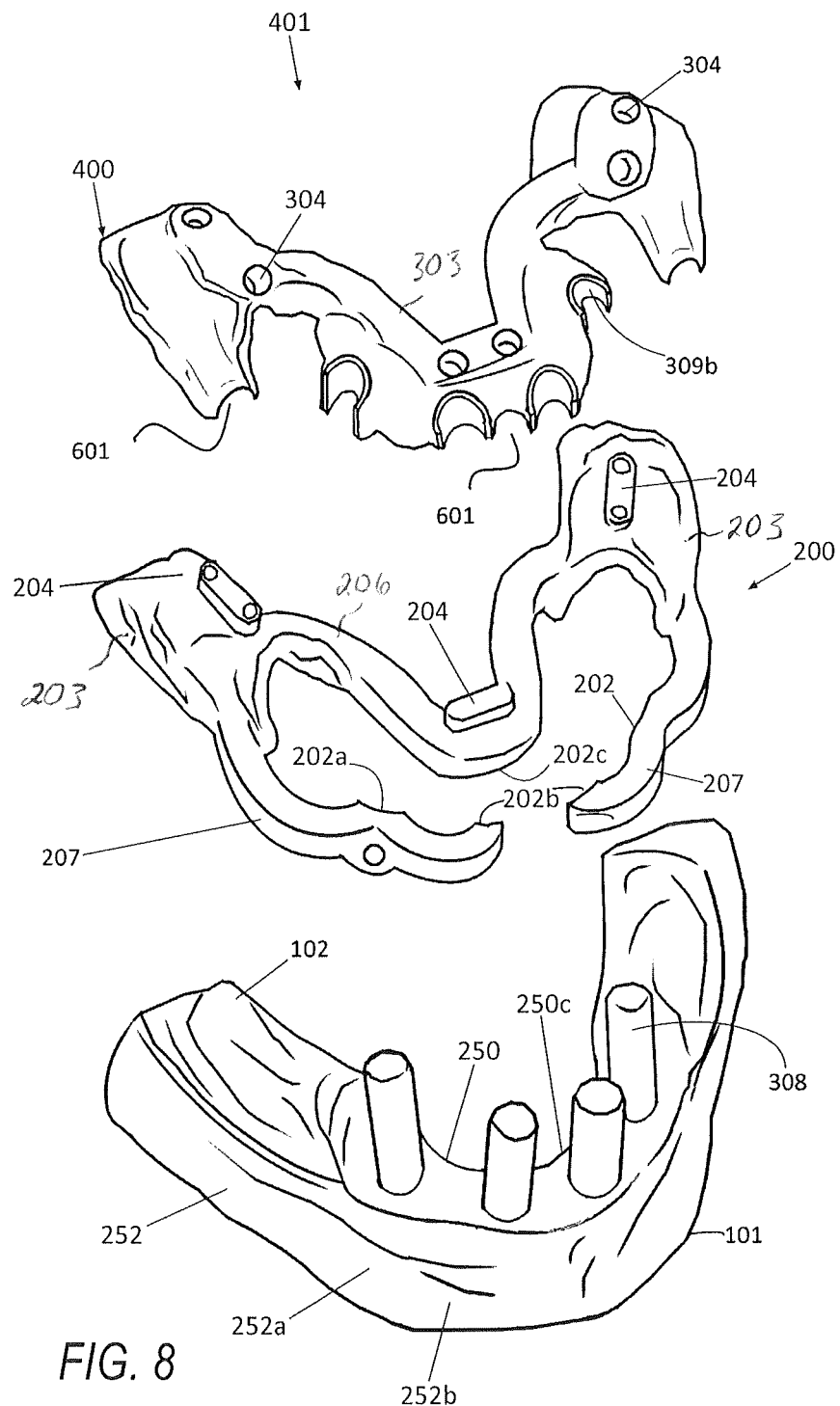
FIG. 8 is an exploded perspective view of the FIG. 6D drill guide assembly.

FIG. 8 is an exploded view of a two part surgical drill guide assembly 401 that is shown in FIG. 6D. The assembly consists of the surgical drill guide section 400 and the interlocking base 200. Collectively, the drill guide section 400 and base 200 can be snapped together and strategically placed relative to the lower jaw 101 which, in this instance, is a physical diagnostic anatomical model of a lower jaw for a human being. The base 200 has a base member 203 at a rearward portion, a first outwardly extending clasping or stabilizing arm 207, and a second arm 206 that extends from the base member 203. The arms have flattened portions and are resilient for placing a force on a jaw. The base 200 is operable to be received on the lower jaw 101 and located relative to the interior 250 and exterior 252 surfaces of the lower jaw 101. In particular, the base 200 further has lateral contacts 202 at internal locations, which are strategically located to impinge upon exterior surface 252 of the lower jaw 101. For example, lateral contact 202a is operable to impinge upon exterior contact 252a. Likewise, lateral contact 202b is designed to strategically impinge upon contact surface 252b in two locations relative to the exterior surface 252 of the lower jaw 101. Likewise, lateral contact 202c is located on an outwardly extending portion of the base frame 200, and is operable to engage interior surface 250c of the lower jaw 101. These contact points, and others, are designed to impinge forces 20 (See FIGS. 2A, 2E and 6C) for aiding and positioning, the base frame 200 relative to the lower jaw 101.

Once the base frame 200 has been positioned relative to the lower jaw 101, the surgical drill guide section of 400 has receptacles that are snapped to interlocking connectors 204 that, in the exemplary model, are positioned at three locations about the base frame 200. It will be appreciated that more, or fewer, interlocking connectors 204 can be provided. The locking fit between the interlocking connectors 204 and the corresponding female receptacles that are on the underneath side of the surgical drill guide section 400, create a snap-fit type connection. This snap-fit configuration provides for ease of separability of the drill guide section 400 and the base frame 200, as well as provides a self-centering locating arrangement for making sure the assembly 401 is properly fit together. The drill guide section 400 includes a flattened center portion 303 that has a plurality of bushings 309a or 309b extending through the flattened portion. The drill guide section 400 further may have water escape holes 304, along with the open face drill guide bushings 309b, as well as a separation feature or openings 601 at three locations, which aid in separating the drill guide section 400 and the base frame 200. The openings 601 are sufficient to allow a device, for example a dental instrument, to be inserted between the drill guide section 400 and the base frame 200, so as to allow ease of separation of the two components.

The open face drill guide bushings 309b provide a guide mechanism for receiving positioning pins 308. The bushings are preferably made of metal and they are anchored in the guide section 400. The positioning pins 308 may be made of metal or hard plastic and are placed into the planned osteotomies within the lower jaw anatomical diagnostic model 101 and are configured to receive the bushings 309b, which helps align the drill guide 400 relative to the jaw 101. At the surgery, drill guide bushings guide the drills to create osteotomies for implant placement.

Figure 9:
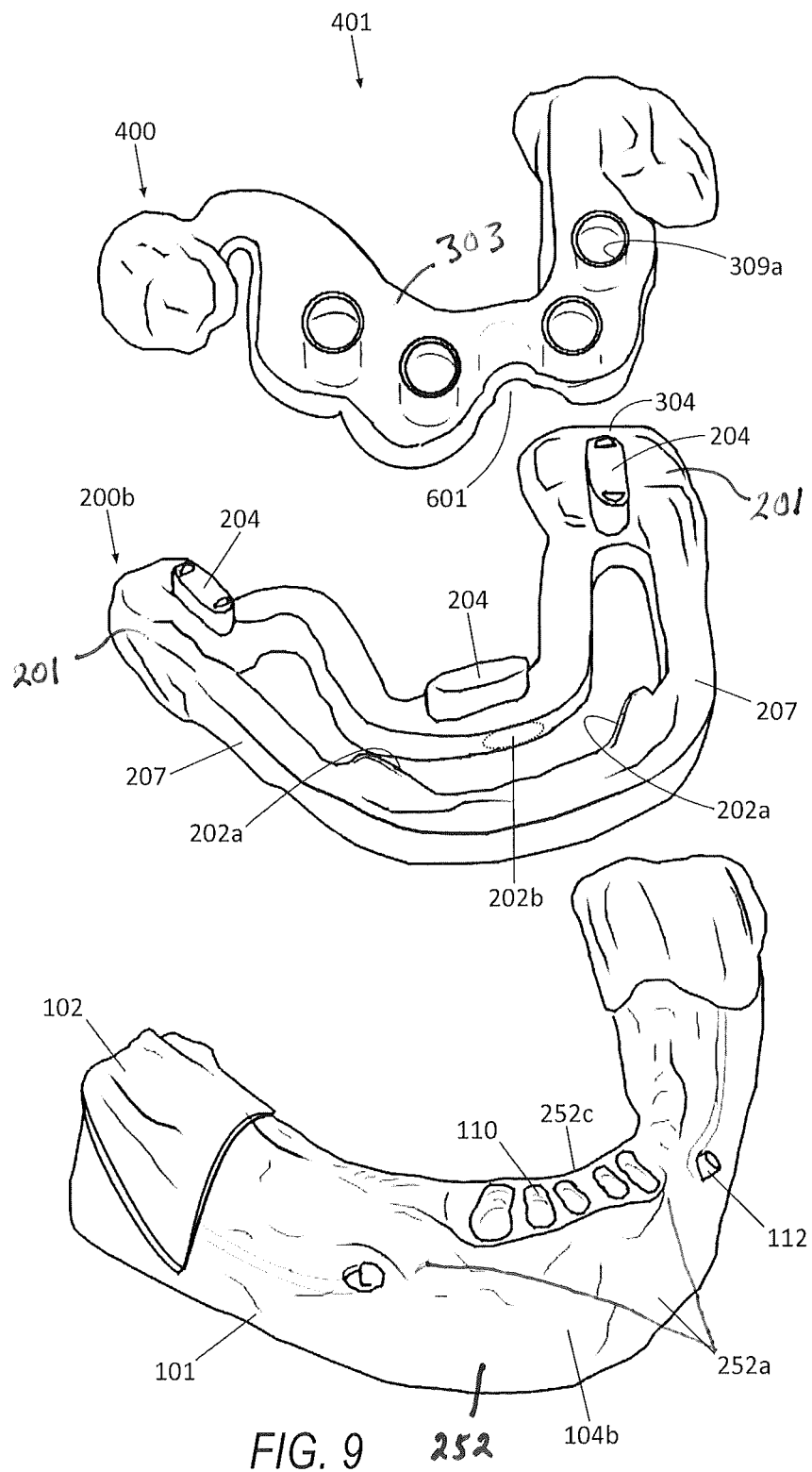
FIG. 9 is an exploded perspective view of another exemplary drill guide assembly.

FIG. 9 illustrates another exemplary drill guide assembly 401 including a drill guide section 400 and a base frame 204b, which also works as a bone reduction jig. The assembly 401 can be positioned relative to exposed bone area 104b of a lower jaw 101, which, in this visual, is a diagnostic anatomical lower jaw model. This particular lower jaw model 101 includes extracted teeth sockets 110, which can be either recently extracted teeth or digitally simulated planned teeth extraction, a gum tissue area 102, and nerve endings 112. The base frame 200b has interlocking connectors 204 formed on the upper surface of the base frame 200b that can be integrally molded to the base frame 200b. Lateral contacts 202a and 202b are positioned about an interior surface of the clasping arm 207 and form pressure points for impinging upon exterior surface 252 of the lower jaw 101 at points 252a, and 252c, respectively.

The surgical drill guide section 400 is shown ready to be positioned and connected to the base frame 200b. Drill guide bushings 309a are provided within holes for receiving positioning pins 308. An opening 601 is provided to help in separating the drill guide section 400 from the base frame 200b.

Figure 10:
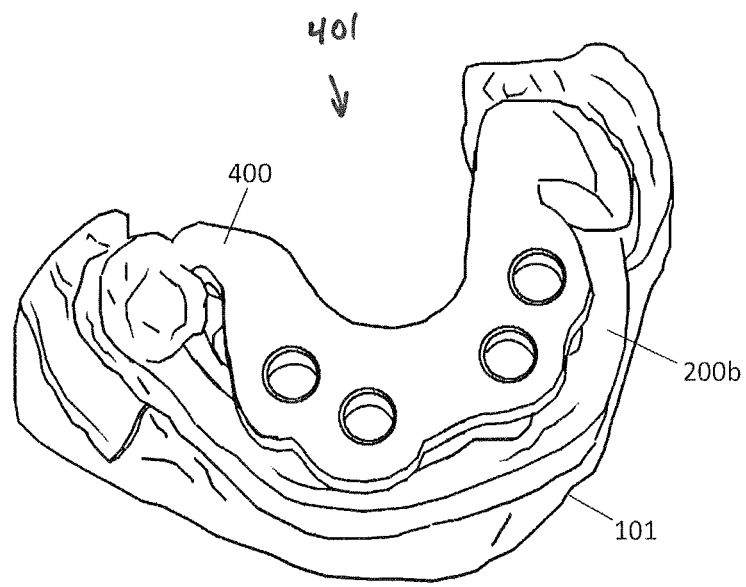
FIG. 10 is the FIG. 9 drill guide assembly in assembled form.

FIG. 10 illustrates the FIG. 9 surgical drill guide assembly 401 in an assembled condition. The drill guide 400 is shown in place relative to the base frame 200b which in turn, is positioned relative to the lower jaw 101.

Figure 11:
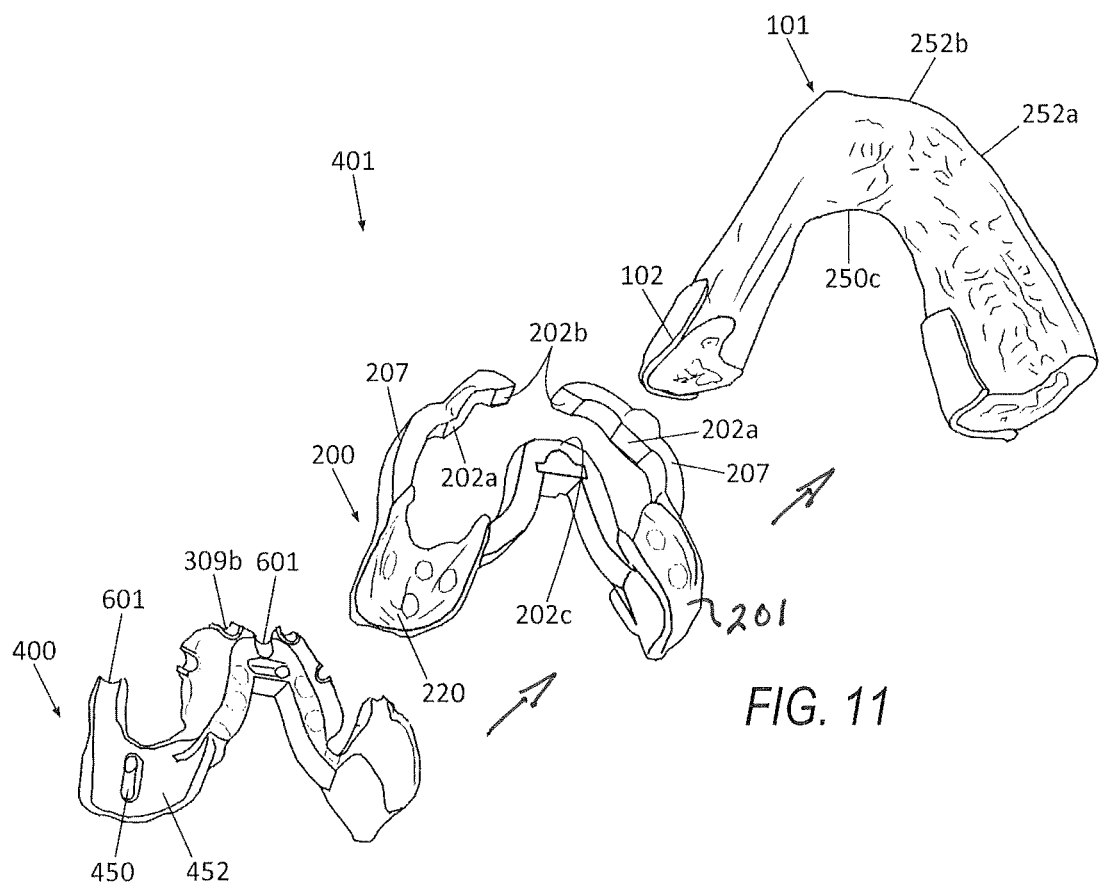
FIG. 11 is a bottom perspective exploded view of the FIG. 8 assembly.

FIG. 11 illustrates a bottom perspective view of the FIG. 6 surgical drill guide assembly 401. From this perspective, the underside of the base frame 200 and the drill guide section 400 can be more readily observed. The lower jaw 101 is shown with gum tissue 102. The Base frame 200 has scalloped or saddle shaped tissue contact portions 220 that are received by the gum tissue areas 102 of the lower jaw 101. The clasping arm 207 has impinging areas 202a and 202b that impinge upon surfaces 252a and 252b, respectively, of the jaw 101. Likewise, impinging surface 202c impinges upon corresponding internal surface 250c of the jaw 101 so as to provide an inwardly impinging force 20 as previously depicted in FIG. 6C.

The surgical drill guide section 400 has receptacles on the underside surface 452 that are operable to lockingly engage with interlocking connectors 204 (FIG. 9) of the base frame 200. Openings 601 provide a gap between the surgical drill guide 400 and the base frame 200 so as to allow for ease of separation between these two components. The recess 450 is slightly larger in physical configuration than the interlocking connector 204. The interlocking connector 204 is sufficiently resilient, as is the receptacle 450, so as to provide a positive snap-fit locking configuration between the components 400 and 200. Once together, an interlocked assembly 401 is created, which can be easily aligned relative to the jaw 101.

FIG. 12 illustrates a perspective view of the base frame 200, which is functioning here as a bone reduction jig, being positioned relative to the lower jaw 101 in the context of a mouth 150. It depicts the lower jawbone having a shaved section 152 according to the clasping arm portion of the base frame 200. Extracted teeth sockets 154 are present and depict the location of the extracted teeth. An interlocking connector 204 is shown and is operable and ready to receive the surgical drill guide section 400 (not shown).

Figure 13:
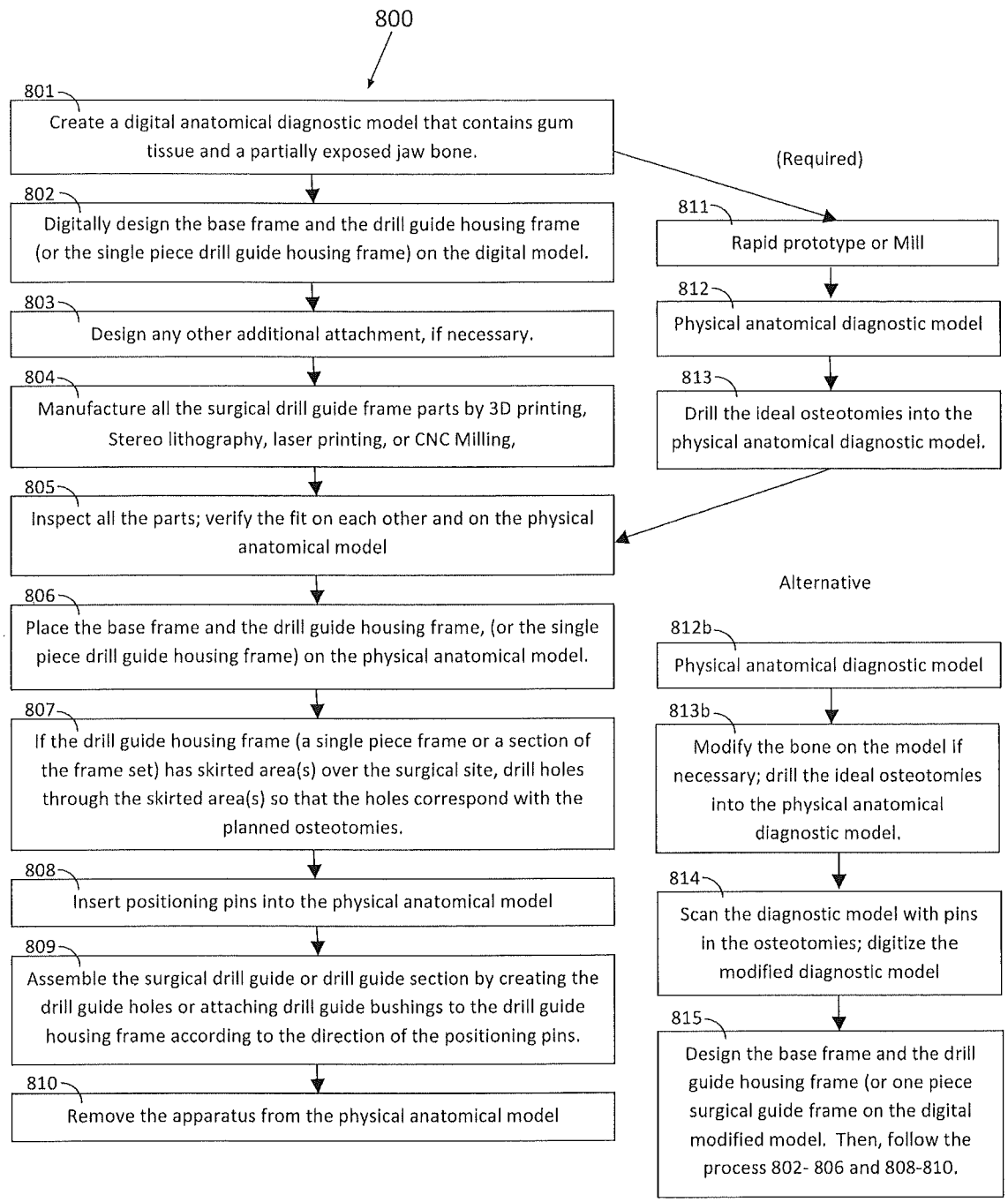
FIG. 13 is a diagram of the edentulous surgical drill guide manufacturing process for a model based implant placement planning.
Figure 14:
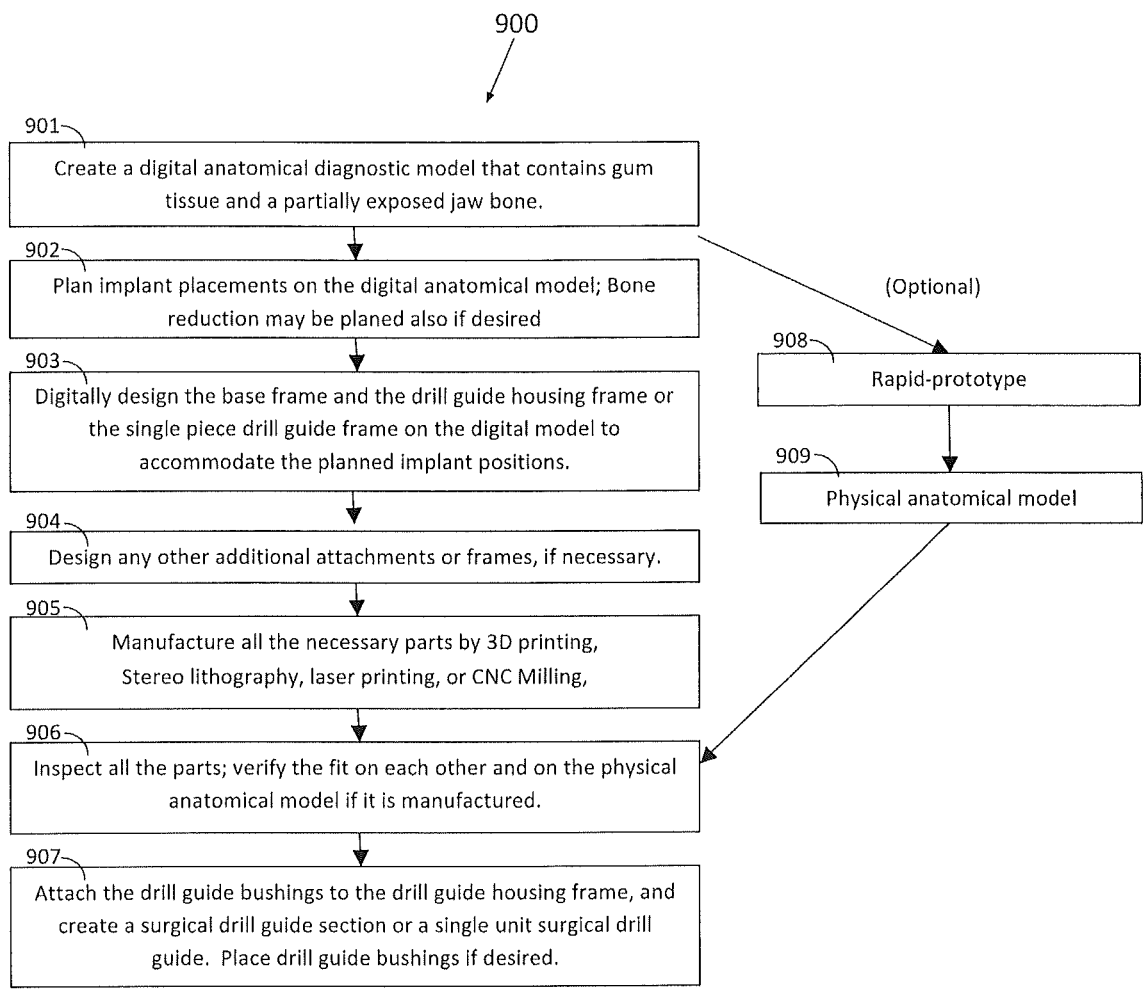
FIG. 14 is a diagram of the edentulous surgical drill guide manufacturing process for a digital implant placement planning.

FIG. 13 and FIG. 14 show different manufacturing methods of using an edentulous surgical drill guide or assembly 401. FIG. 13 illustrates a model based implant placement planning method 800 and FIG. 9 illustrates a digital implant placement planning method 900. Both methods start with a digital anatomical diagnostic model, with partially exposed jawbone 101 in the area of interest, in a file format such as STL that allows reverse engineering and 3D modeling 801 and 901. The digital anatomical diagnostic model 801 can be obtained by accurately aligning the surface scan data of the patient's mouth or dental cast and the tomography scan data that is volume rendered and converted to a compatible file format. Since all the devices are patient specific, the design and features of the apparatus is planned according to the patient's oral structure, bone condition, and the surgical needs. Although the apparatus can be created as one single surgical guide as described in the diagram in FIG. 7, the same or similar procedure may be applied when using a multiple piece guide.

In both methods, a technician digitally designs the base frame 200, and the drill guide housing frame 300, along with additional frames and attachments, if any, using reverse engineering software program such as Geomagic, Radidform, and 3 Matics, optionally combined with 3D modeling software such as Rhinoceros 3D and Solidworks (See steps 802, 902, 803 and 903). The base frame 200 (FIG. 2) can be designed first on the digital model with partially exposed bone just in the area of the surgical site 802 and 903 and then the drill guide housing frame section 300 (FIG. 3) can be designed on both the digital anatomical diagnostic model and the base frame (802 and 902). By doing so, the surgical guide can be designed to obtain better fit and stability, because 1) it avoids bone contact in the areas where the density of the bone is too close to that of the soft tissue for its contour to be accurately defined in the CT images when the bone is porous, and 2) it also clasps onto rigid bone areas instead of contacting the malleable tissue surface alone. Subsequently, if additional frames or attachments are needed, they can be designed to fit on the base frame 200 and/or the surgical drill guide housing frame 300 according to the part's function 803 and 903. Some of the features and functions of the apparatus are the same or similar for the model based implant placement planning or the digital implant placement planning. However, several differences may be found in features and methods between for these two situations.

FIG. 13 illustrates a workflow 800 of a model based surgical planning. When the implant placement is planned on an aligned physical anatomical diagnostic model 812 created by rapid prototyping 811 the digital model 801, the technician needs to design the drill guide housing frame or housing frame section 300 on the digital anatomical diagnostic model without knowing the exact plan of implants' positioning. Naturally, the device is designed as a base structure of the surgical guide that will be assembled manually on the physical anatomical model. Thus, the device often has the skirted area 301 (FIG. 3B) that extends over the intended site so that it is easier for the clinician or technician to assemble the surgical drill guide later on a physical anatomical diagnostic model (See steps 806-809). Similarly, other special parts that work on the physical model may also be designed to aid the surgical guide assembly. Meanwhile, a physical anatomical diagnostic model is manufactured by rapid prototyping or CNC milling (See steps 811-812), and ideal osteotomies are simulated on the physical anatomical diagnostic model by a qualified clinician (Step 813). Alternatively, the modified anatomical diagnostic model (step 812b) with positioning pins placed into the osteotomies can be digitized by surface scanning (Step 814), and the drill guide 200, 400 or 700 may be designed on the modified digital anatomical diagnostic model. If bone reduction is planned on a physical anatomical diagnostic model then the doctor can drill the ideal osteotomies into the physical model, (See step 813b).

After all the parts are designed on the digital diagnostic model, they are manufactured by rapid prototyping such as 3D printing and stereolithography or CNC milling 804, cleaned, inspected, and verified on the physical anatomical model 805. Place the base frame and the drill guide housing frame 200 on the physical anatomical model 100, as shown in step 806.

If the drill guide housing frame has skirted areas 301 (FIG. 3B) over the surgical site, drill holes may be placed through the skirted areas 301 with a hand piece or drill 312 (FIG. 3C) so that the holes correspond with the planned osteotomies. Since the drill guide housing frame is usually made with a transparent or semi-transparent material, the simulated osteotomies on the model is visible thorough the thin skirted areas 301, and corresponding holes can be made. Positioning pins 308 may be inserted into the osteotomies on the anatomical model through the holes of the skirted areas 808. Drill guide bushings 309 may be placed with respect to the positioning pins 308 and the bushings' distance may be set from the oral structure according to the preference. As briefly described above, the top or the bottom of the skirted areas 301 may be set at, below or above the gum tissue surface 102.

Alternatively, the bottom of the skirted areas 301 may be made to contact the exposed bone. If the diameter of holes on the skirt is close to the inner diameter of the drill guide bushing, the bushing can rest on the skirted areas. The holes of the skirted areas 301 may also be made larger so that extra parts to control the height can be inserted onto the positioning pins 305. It should also be noted that the drill guide housing frame 300 may be configured to accommodate various types of interchangeable drill guide bushings as well as most of depth control surgical guide system parts sold by various implant companies. After the positions are set, the bushings maybe attached to the drill guide housing frame with light cured composite or other adhesive materials 809. Additional light cured composite may be added to the frame to increase the rigidity of the device. Light cured composite may be added around the positioning pins on the skirted areas 301 instead of bushings to conform drill guide holes or slots. When finished, the positioning pins may be removed from the physical anatomical model 810. The skirted area can be then trimmed by a hand piece as previously described. Additional drill guide frames, if any, can be made by repeating the process. With a model based implant placement system, it may also be possible to manually create a surgical drill guide that clasps the gum tissue and the jawbone with similar features without any digitally designed frame structures. It should be noted that the skirted area may not be necessary if the anatomical diagnostic model is surface scanned after the doctor drills the osteotomies, and the apparatus is designed on the modified digital model.

FIG. 14 illustrates a flowchart of digital surgical planning. When the implant placement is planned digitally on an aligned digital anatomical diagnostic model 902 as illustrated in FIG. 14, the creation of physical anatomical diagnostic model may be optional 908, 909. In this case, the technician can design the drill guide housing frame according to the simulated osteotomies on the digital anatomical model. Thus, there may be no need to create any skirted area. The support structure and receptor sites for the drill guide bushings can be digitally designed 903 so that the device is ready to receive the parts after prototyping. If any drill guide bushing parts with depth control function are going to be used, the device can be designed to receive those parts at the exact locations to accommodate the function 904. If the jaw bone 101 is reduced on the digital anatomical diagnostic model, the base frame 200 may be designed to function as a bone reduction jig.

Similar to the method for a model based implant placement system, the drill guide housing frame 300 is manufactured, along with the base frame and other additional frames and accessories, by rapid prototyping or CNC milling 905. After cleaning and inspection 906, the preferred drill guide bushings 309 can be placed into the drill guide frame 300 and secured by light cured composite or other adhesive material 907. For some type of drill guide bushings (309) adhesives may not be needed. The drill guide may also be created with built-in drill guide holes or slots without any separate parts if the device is made of an appropriate harder material such as metal.

Figure 15:
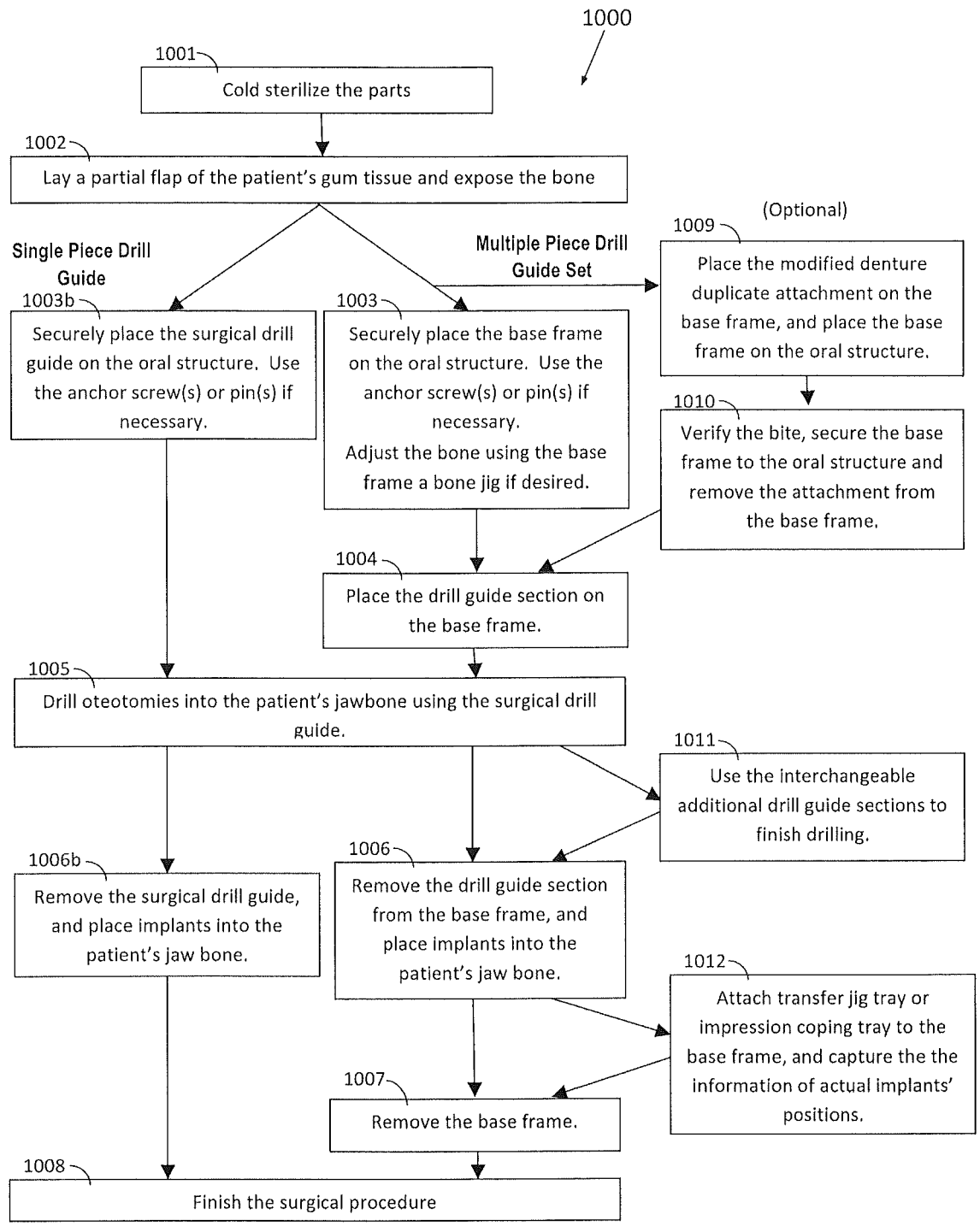
FIG. 15 is a diagram of how to utilize the edentulous surgical drill guide during the surgery.

FIG. 15 illustrates a flowchart of how the apparatus 401 can be utilized 1000 during an implant placement surgery. It will be appreciated that the steps can be modified, yet remain within the spirit of the exemplary embodiments herein. It should be noted that there are many variations to the workflow, and this chart is not intended to teach the surgical procedure itself. As is the case with the explanation of diagrams in FIG. 13 and FIG. 14, the following explanation is directed to a multiple piece drill guide system 401.

Prior to the surgery, all the parts of the drill guide set 401 are properly sanitized according to the material's requirement. For example, if the parts are rapid prototyped with resin, cold sterilization methods may be appropriate. However, heat sterilization may be used for different materials with high temperature tolerance 1001. Lay a partial flap of the patient's gum tissue to expose the jawbone in the area of interest 1002. In rare occasions, the surgeon may choose to flap only the areas that the bone clasping contact portions of the devise will contact with, leaving the gum tissue over the implant sites. The base frame 200 or the single piece surgical drill guide 300 may be securely placed on the oral structure 100 and in contact with both gum tissue and the exposed bone (See steps 1003 and 1003b). Additional attachments may be added to the device for bone clasping. Depending on the patient's oral structure, anchor screws or pins may be used for securing the position of the device. Bone adjustment or bone grafting may be done before or after the placement of the base frame 200. If the bone adjustment is needed, the base frame may be used as a jig or an additional bone adjustment jig can be attached to the base frame 200 for this process.

Optionally, a modified denture duplicate attachment 500 (FIG. 5) can be used on the base frame 200. In that case, verify the device's positioning with bite to secure the base frame 200 to the oral structure, and then remove the attachment portion, leaving the base frame 300 on the oral structure 1009 and 1010.

After the base frame is securely placed, attach the drill guide section 300 to the base frame 200 (step 1004) in order to drill osteotomies into the jawbone (step 1005). The interchangeable additional drill guide sections may be used to complete the osteotomies 1011. When finished, the drill guide section 400 may be removed from the base frame (200), and the implants may be placed into the jawbone (see step 1006 and 1006b). Should a certain type of surgical guide tube system be adopted into the drill guide frame 300, the surgeon may place the implants through the drill guide tube bushings 1009 prior to the removal of the drill guide section 400.

The surgeon may choose to take a fixture level index for the record of implant positions at this point. In that case, he/she may be able to do so by altering the surgical guide section 400 into a transfer jig tray or by using a separate transfer jig tray that attaches to the base frame 200 (See step 1012). One advantage of utilizing the drill guide section 400 is that the actual positioning information can be easily transferred back to the physical anatomical model. The model can be adjusted, if necessary, and the prosthesis can be created on it without making a separate brand new model.

After the base frame is removed 1007 the surgeon can complete the surgery by placing cover screws or healing caps, and suturing the gum tissue over the cover screw or around the healing caps. Alternatively, the immediate loading procedure may be followed, and the prosthesis that had been designed on the digital or the physical anatomical model can be placed 1008.

What is claimed as new and desired to be protected by Letters Patent of the United States is:

1. A method, comprising:
   obtaining a digital preoperative dental model of a patient;
   creating a digital, 3D design of a guide appliance set on the digital preoperative dental model according to a surgical plan for the patient;
   storing the design of the guide appliance set in a computer-aided manufacturing (CAM) compatible file format; and
   manufacturing at least a portion of the designed guide appliance set via a CAM method using the stored design of the guide appliance set;
   wherein creating the design of the guide appliance set includes:
      designing a base frame configured to engage an oral structure of the patient without obstructing a planned surgical site region of an alveolar ridge of the patient;
      designing an uppermost surface of the base frame to, at least in an area adjacent to the planned surgical site region, terminate below the alveolar ridge when the base frame is engaged with the oral structure;
      designing at least one attachment that is releasably attachable to the base frame, the at least one attachment designed to facilitate performance of at least a portion of a dental surgery; and
      designing the at least one attachment to obstruct at least a portion of the alveolar ridge and to be fully received in a mouth of the patient when attached to the base frame.

2. The method of claim 1, wherein:
   obtaining the digital preoperative dental model includes obtaining preoperative scan data of the oral structure of the patient; and
   the preoperative scan data includes a plurality of preoperative scan coordinates collected from at least one of:
      a tomography of the oral structure of the patient;
      a topography of the oral structure;
      a topography of a dental impression of the oral structure;
      a topography of a removable prosthesis of the patient; and
      a tomography of the oral structure when the removable prosthesis is disposed thereon.

3. The method of claim 1, wherein designing the base frame includes providing the base frame with an opening for accepting at least one anchor via which the base frame is connectable to the oral structure.

4. The method of claim 1, wherein:
   the at least one attachment includes a plurality of attachments; and
   designing the plurality of attachments includes:
      designing a first attachment of the plurality of attachments as a bone adjustment jig configured to facilitate vertically reducing at least a portion of the alveolar ridge in the surgical site region during surgery;
      designing a second attachment of the plurality of attachments as a drill guide configured to facilitate drilling a hole at a planned dental implant site;
      designing a third attachment of the plurality of attachments as a transfer jig configured to facilitate taking a positional index of installed implants;

designing a fourth attachment of the plurality of attachments as a positioning attachment configured to facilitate positioning the base frame in the oral structure at a predetermined position;
designing a fifth attachment of the plurality of attachments as at least one of an impression coping tray and an implant pick up impression tray; and
designing a sixth attachment of the plurality of attachments as a modified denture attachment.

5. The method of claim 1, wherein the at least one attachment is a modified denture attachment configured to facilitate positioning the base frame in the oral structure at a predetermined position.

6. The method of claim 1, wherein the at least one attachment is designed as at least one of:
a bone adjustment jig configured to facilitate vertically reducing at least a portion of the alveolar ridge in the surgical site region during surgery;
a drill guide configured to facilitate drilling a hole at a planned dental implant site;
a positioning attachment configured to facilitate positioning the base frame in the oral structure at a predetermined position;
a transfer jig configured to facilitate taking a positional index of installed implants;
an implant pick up impression tray;
an impression coping tray; and
a modified denture attachment.

7. The method of claim 1, wherein designing the base frame includes designing a plurality of base frame pieces that are at least one of (i) connectable to one another via a set of detachable inter-locking connectors and (ii) connected to one another via a hinge.

8. The method of claim 1, wherein the digital preoperative dental model includes at least one of (i) a simulated bone reduction, (ii) a simulated extraction of at least one tooth, and (iii) a simulation of at least one drill hole disposed in the planned surgical site region.

9. The method of claim 1, further comprising manufacturing the digital preoperative dental model via a CAM method.

10. The method of claim 1, further comprising:
obtaining the guide appliance set;
positioning the base frame on the oral structure of the patient;
vertically reducing at least a portion of the alveolar ridge in the surgical site region while the base frame is positioned on the oral structure;
attaching the at least one attachment to the base frame; and
when the at least one attachment is attached to the base frame, using the at least one attachment as a guide while performing a portion of the dental surgery.

11. The method of claim 1, further comprising creating a postoperative dental model via transferring information from a production of the at least one attachment to at least one preoperative dental model, wherein the transferred information is derived from a positional index of at least one installed dental implant of the patient that was recorded using the production of the at least one attachment.

12. The method of claim 1, wherein:
the planned surgical site region of the alveolar ridge includes a plurality of planned dental implant sites; and
the base frame is designed to facilitate vertically reducing the planned surgical site region of the alveolar ridge while the base frame is positioned on the oral structure.

13. A method, comprising:
obtaining a guide appliance set designed based on a digital preoperative dental model of a patient and a surgical plan for the patient, the guide appliance set including (i) a base frame configured to engage an oral structure of the patient without obstructing a planned surgical site region of an alveolar ridge of the patient, the base frame having an uppermost surface that, at least in an area adjacent to the planned surgical site region, is sized to terminate below the alveolar ridge when the base frame is engaged with the oral structure and (ii) at least one attachment that is releasably attachable to the base frame, the at least one attachment configured to facilitate performance of at least a portion of a dental surgery;
positioning the base frame on the oral structure of the patient;
attaching the at least one attachment to the base frame such that the at least one attachment obstructs at least a portion of the alveolar ridge and is fully received in a mouth of the patient; and
when the at least one attachment is attached to the base frame, using the at least one attachment while performing a portion of the dental surgery.

14. The method of claim 13, wherein at least one of:
the at least one attachment includes a positioning attachment, and the method further comprises (i) attaching the positioning attachment to the base frame and (ii) adjusting the base frame to a desired position relative to the oral structure via placing the positioning attachment on the oral structure;
the at least one attachment includes a transfer jig configured to facilitate taking a positional index of installed implants, and the method further comprises taking a positional index of at least one installed dental implant with the transfer jig; and
the at least one attachment includes a drill guide configured to facilitate positioning a drill at a planned dental implant site, and the method further comprises (i) attaching the drill guide to the base frame, (ii) guiding the drill to the planned dental implant site using the drill guide, and (iii) drilling a hole in the oral structure at the planned dental implant site using the drill.

15. The method of claim 13, wherein:
the digital preoperative dental model is designed based on preoperative scan data of the patient;
the guide appliance set includes a physical preoperative dental model designed based on the preoperative scan data of the patient; and
the preoperative scan data includes preoperative scan coordinates collected from at least one of:
a tomography of the oral structure of the patient;
a topography of the oral structure;
a topography of a dental impression of the oral structure;
a topography of a removable prosthesis of the patient; and
a tomography of the oral structure when the removable prosthesis is disposed thereon.

16. The method of claim 13, further comprising vertically reducing at least a portion of the alveolar ridge in the surgical site region while the base frame is positioned on the oral structure, wherein vertically reducing the alveolar ridge includes at least one of:
using the base frame as a guide while vertically reducing the alveolar ridge in the surgical site region; and attaching a bone adjustment jig configured to facilitate surgical modification of at least a portion of the alveolar ridge in the surgical site region to the base frame and using the bone adjustment jig as a guide while vertically reducing the alveolar ridge in the surgical site region, the at least one attachment including the bone adjustment jig.

17. A method, comprising:
obtaining a digital preoperative dental model of a patient;
designing a guide appliance set on the digital preoperative dental model according to a surgical plan for the patient;
storing the design of the guide appliance set in a computer-aided manufacturing (CAM) compatible file format; and
manufacturing at least a portion of the designed guide appliance set via a CAM method using the stored design of the guide appliance set;
wherein designing the guide appliance set includes:
  designing a base frame configured to engage an oral structure of the patient without obstructing a planned surgical site region of an alveolar ridge of the patient, the planned surgical site region of the alveolar ridge includes a plurality of planned dental implant sites;
  designing an uppermost surface of the base frame to, at least in an area adjacent to the planned surgical site region, terminate below the alveolar ridge when the base frame is engaged with the oral structure;
  designing at least one attachment that is releasably attachable to the base frame, the at least one attachment designed to facilitate performance of at least a portion of a dental surgery; and
  designing the at least one attachment to be fully received in a mouth of the patient when attached to the base frame;
wherein at least one of:
  the base frame is designed to facilitate vertically reducing the planned surgical site region of the alveolar ridge while the base frame is positioned on the oral structure; and
  the at least one attachment is designed as a bone adjustment jig configured to facilitate vertically reducing the planned surgical site region of the alveolar ridge while the base frame is positioned on the oral structure and the bone adjustment jig is attached to the base frame.

18. A method, comprising:
obtaining a guide appliance set designed based on a digital preoperative dental model of a patient and a surgical plan for the patient, the guide appliance set including (i) a base frame configured to engage an oral structure of the patient without obstructing a planned surgical site region of an alveolar ridge of the patient, the base frame having an uppermost surface that, at least in an area adjacent to the planned surgical site region, is sized to terminate below the alveolar ridge when the base frame is engaged with the oral structure and (ii) at least one attachment that is releasably attachable to the base frame, the at least one attachment configured to facilitate performance of at least a portion of a dental surgery;
positioning the base frame on the oral structure of the patient;
vertically reducing at least a portion of the alveolar ridge in the surgical site region while the base frame is positioned on the oral structure;
attaching the at least one attachment to the base frame such that the at least one attachment obstructs at least a portion of the alveolar ridge and is fully received in a mouth of the patient; and
when the at least one attachment is attached to the base frame, using the at least one attachment while performing a portion of the dental surgery;
wherein vertically reducing the alveolar ridge includes at least one of:
  using the base frame as a guide while vertically reducing the alveolar ridge in the surgical site region; and
  attaching a bone adjustment jig configured to facilitate surgical modification of at least a portion of the alveolar ridge in the surgical site region to the base frame and using the bone adjustment jig as a guide while vertically reducing the alveolar ridge in the surgical site region, the at least one attachment including the bone adjustment jig.

19. A method of creating a guide appliance set, comprising:
obtaining preoperative scan data of an oral structure of a patient, the preoperative scan data including a plurality of preoperative scan coordinates collected from at least one of:
  a tomography of the oral structure of the patient;
  a topography of the oral structure;
  a topography of a dental impression of the oral structure; and
  a topography of a removable prosthesis of the patient;
creating a digital, 3D preoperative model based on the preoperative scan data and a surgical plan for the patient;
creating a digital, 3D guide appliance set positionable on the digital preoperative model according to the surgical plan;
storing the digital guide appliance set in a computer-aided manufacturing (CAM) compatible file format to create a CAM-ready guide appliance set file; and
manufacturing a physical production of at least a portion of the digital guide appliance set using the CAM-ready guide appliance set file;
wherein creating the digital guide appliance set includes:
  creating a base frame configured to engage the oral structure of the patient without obstructing a planned surgical site region of an alveolar ridge of the patient;
  creating an uppermost surface of the base frame to, at least in an area adjacent to the planned surgical site region, terminated below the alveolar ridge when the base frame is engaged with the oral structure;
  creating at least one attachment that is releasably attachable to the base frame, the at least one attachment designed to facilitate performance of at least a portion of a dental surgery; and
  creating the at least one attachment to be fully received in a mouth of the patient when attached to the base frame; and
wherein creating the at least one attachment includes at least one of:
  creating a bone adjustment jig configured to facilitate vertically reducing at least a portion of the alveolar ridge in the surgical site region during surgery;
  creating a surgical drill guide configure to facilitate drilling at least one hole at a planned dental implant site;
  creating a positioning attachment configured to facilitate positioning the base frame on the oral structure at a predetermined position; and creating a transfer jig configured to facilitate taking a positional index of installed implants.

20. The method of claim 19, wherein creating the at least one attachment further includes creating a modified denture attachment.

* * * * *